United States Patent
Choi et al.

(10) Patent No.: US 12,128,585 B2
(45) Date of Patent: Oct. 29, 2024

(54) DEVICE FOR MANUFACTURING LARGE AMOUNT OF POLYMERIC MICRO-SCAFFOLDS

(71) Applicants: INDUSTRY FOUNDATION OF CHONNAM NATIONAL UNIVERSITY, Gwangju (KR); BIOT KOREA INC., Gwangju (KR)

(72) Inventors: Eun Pyo Choi, Gwangju (KR); Jong Oh Park, Gyeonggi-do (KR); Chang Sei Kim, Gwangju (KR); Byung Jeon Kang, Gwangju (KR); Seok Jae Kim, Gwangju (KR); Gwang Jun Go, Gwangju (KR); Yeong Jun Chang, Seoul (KR)

(73) Assignees: INDUSTRY FOUNDATION OF CHONNAM NATIONAL UNIVERSITY, Gwangju (KR); BIOT KOREA INC., Gwangju (KR)

( * ) Notice: Subject to any disclaimer, the term of this patent is extended or adjusted under 35 U.S.C. 154(b) by 1099 days.

(21) Appl. No.: 16/976,413

(22) PCT Filed: Mar. 26, 2019

(86) PCT No.: PCT/KR2019/003482
§ 371 (c)(1),
(2) Date: Aug. 27, 2020

(87) PCT Pub. No.: WO2019/190155
PCT Pub. Date: Oct. 3, 2019

(65) Prior Publication Data
US 2021/0379799 A1    Dec. 9, 2021

(30) Foreign Application Priority Data

Mar. 27, 2018 (KR) .................. 10-2018-0035464

(51) Int. Cl.
*B01J 2/04* (2006.01)
*B29C 31/02* (2006.01)
(Continued)

(52) U.S. Cl.
CPC ............... *B29C 31/04* (2013.01); *B01J 2/04* (2013.01); *B29C 31/02* (2013.01); *B29C 67/202* (2013.01);
(Continued)

(58) Field of Classification Search
CPC ....... B29C 31/04; B29C 31/02; B29C 67/202; C08J 9/0061; C08J 9/26; C08J 2205/044;
(Continued)

(56) References Cited

U.S. PATENT DOCUMENTS

2011/0200678 A1    8/2011   Hwang et al.

FOREIGN PATENT DOCUMENTS

KR         10-0924236 B1    10/2009
KR     10-2011-0022096 A     3/2011
(Continued)

OTHER PUBLICATIONS

Extended European Search Report from corresponding European Patent Application No. 19774284.4, issued on Apr. 8, 2021.
(Continued)

*Primary Examiner* — Armand Melendez
(74) *Attorney, Agent, or Firm* — Harness, Dickey & Pierce, P.L.C.

(57) ABSTRACT

The present invention relates to a manufacturing device for manufacturing a large amount of micro-scaffolds for a long period of time such that stable and uniform particles can be fabricated. The manufacturing device comprises: a first solution storage portion for storing a polymer support structure solution; a second solution storage portion for storing an emulsifier solution; a gas storage portion connected to each
(Continued)

of the first solution storage portion and the second solution storage portion; a pressure control portion for controlling the pressure of the transporting gas flowing into the first solution storage portion and the second solution storage portion from the pressurization portion, respectively; a scaffold injector portion for receiving the polymer support structure solution and the emulsifier solution provided by the transporting gas, respectively; and a scaffold generating portion for receiving the scaffold dispersion discharged through the scaffold injection portion.

12 Claims, 4 Drawing Sheets

(51) Int. Cl.
  *B29C 31/04* (2006.01)
  *B29C 67/20* (2006.01)
  *C08J 9/00* (2006.01)
  *A61L 27/26* (2006.01)
  *A61L 27/56* (2006.01)
  *B29K 105/04* (2006.01)
  *C08J 9/26* (2006.01)

(52) U.S. Cl.
  CPC ............ *C08J 9/0061* (2013.01); *A61L 27/26* (2013.01); *A61L 27/56* (2013.01); *B29K 2105/041* (2013.01); *C08J 9/26* (2013.01); *C08J 2205/044* (2013.01); *C08J 2329/04* (2013.01); *C08J 2367/04* (2013.01); *C08J 2389/00* (2013.01)

(58) Field of Classification Search
  CPC ............... C08J 2329/04; C08J 2367/04; C08J 2389/00; C08J 9/28; C08J 2201/0464; C08J 2201/0502; C08J 2467/04; C08J 2489/00; A61L 27/26; A61L 27/56; A61L 2400/12; A61L 27/20; A61L 27/222; B29K 2105/041; B29K 2105/04; B81C 99/0015; B81C 2900/02
  See application file for complete search history.

(56) References Cited

FOREIGN PATENT DOCUMENTS

KR 10-1521552 B1 5/2015
KR 10-2015-0108956 A 10/2015

OTHER PUBLICATIONS

Choi, S., et al.; "Uniform Beads with Controllable Pore Sizes for Biomedical Applications", Small., Jul. 19, 2010; 6(14), pp. 1492-1498.
Polymer(Korea), vol. 33, No. 4, pp. 353-357, 2009.
International Search Report from corresponding PCT Application No. PCT/KR2019/003482, dated Jul. 11, 2019.

DEVICE FOR MANUFACTURING LARGE AMOUNT OF POLYMERIC MICRO-SCAFFOLDS

CROSS-REFERENCE TO RELATED APPLICATIONS

This application is a national phase application of PCT Application No. PCT/KR2019/003482, filed on Mar. 26, 2019, which claims benefit of Korean Patent Application No. 10-2018-0035464, filed on Mar. 27, 2018. The entire disclosures of the applications identified in this paragraph are incorporated herein by reference.

TECHNICAL FIELD

The present invention relates to a device for manufacturing a large amount of micro-scaffolds and, more specifically, to a device for manufacturing micro-scaffolds uniform in size on a mass scale.

The present invention was made with the support of the Ministry of Science, ICT, and Future Planning of the Republic of Korea, under Project No. 2016M3A9E9941514, which was conducted under the research subject named "Development and Commercialization of Microstructure Targeting Technique for Cartilage Regeneration Substituent" within the program titled ""Project for Development of Original Technology in conjugation with Campus Medical Startup" by "Chonnam National University Hwasun Hospital" under management of the National Research Foundation of Korea, from 1 Nov. 2016 to 31 Jul. 2021.

BACKGROUND

Tissue engineering is the use of a combination of technologies, based on basic concepts and techniques of bioscience, medical science, and engineering, to maintain, improve, or restore body functions by making substituents for biological tissues and transplanting the substituents into a living body.

In the practice of tissue engineering, cells are separated from a necessary tissue taken from a patient's body, amplified to a degree of necessity through cultivation, seeded into a porous biodegradable polymer matrix, and cultured in vitro for a predetermined period of time to manufacture scaffolds which are then transplanted back into the body.

As such, the scaffold refers to a combination of a physical support and an adhesive substrate, which is designed to allow tissue cells to be cultured in vitro and transplanted in vivo. The scaffold may be fabricated into various shapes as needed.

Particularly, the suitable field to the scaffold is applied is determined depending on the thicknesses of strands formed by spraying biocompatible materials and cells and the sizes of pores formed due to gaps between adjacent strands. Scaffolds can be manufactured to have desired sizes of pores by controlling the condition and environment in which molten biocompatible materials are sprayed.

Methods for preparing porous nano- or microparticles having as large surface areas as possible are of important significance in various fields.

For example, such porous nano- or microparticles can be used to fabricate batteries having a longer lifespan in the electrochemical field and to increase solar power efficiency in the alternative energy field. In the drug delivery field, when porous nano- or microparticles are provided as drug carriers to the surface of which drugs are applied or loaded, their increased surface areas per unit volume allow greater doses per unit, thereby giving maximal therapeutic efficiency at the same volume.

Various products of polymer scaffolds having the advantageous surface area have already been marketed and developed into various shapes according to treatment sites and therapeutic purposes. However, the products are, in the most part, patch type products with a size of ones of centimeters, but do not function as a drug delivery system to be inserted into the body.

Techniques for manufacture of micro-sized polymer scaffolds that can be inserted in vivo have been suggested in various ways. As for polymeric micro-scaffolds, however, their manufacture environments have a great influence on the sizes of the manufactured scaffolds. Even a slight change in the manufacturing condition results in a great difference in the products, which makes it difficult to commercialize such techniques.

Of such manufacturing methods for polymeric micro-scaffolds, the use of a microfluidic channel and a double emulsion in combination has the advantage of allowing the user to control particle and pore sizes as desired and to manufacture polymeric micro-scaffolds suitable for desired purposes, but is disadvantageous in that the products with uniform sizes cannot be manufactured steadily to such an extent as to enable practical production, either.

SUMMARY

Technical Problem

The present invention has been made to solve these problems and a purpose of the present invention is to provide a device for manufacture of polymeric micro-scaffolds, by which polymeric micro-scaffolds with uniform sizes can be manufactured stably in spite of changes of external conditions. In addition, another purpose of the present invention is to provide a method for manufacturing polymeric micro-scaffolds on a mass scale.

Technical Solution

In order to achieve the above purposes, an aspect of the present invention provides a device for manufacture of polymeric micro-scaffolds, the device comprising: a first solution storage part for storing a polymeric support structure solution; a second solution storage part for storing an emulsifier solution; a gas storage part, connected to both the first solution storage part and the second solution storage part, for providing a transporting gas for transporting the polymeric support structure solution and the emulsifier solution; a compression part for applying a pressure to the transporting gas supplied to the first solution storage part and the second solution storage part; a pressure controller for controlling the compression part so as to apply pressures to the transporting gas flowing into the first solution storage part and the second solution storage part, respectively; a scaffold injector for receiving the polymeric support structure solution and the emulsifier solution respectively supplied by the transporting gas and releasing a scaffold dispersion resulting from coupling between the polymeric support structure solution and the emulsifier solution; and a scaffold production part for receiving the scaffold dispersion released from the scaffold injector, removing an organic solvent and a dispersion medium from the scaffold dispersion, and producing polymeric micro-scaffolds.

In the device for manufacture of polymeric micro-scaffolds according to the present invention, the polymeric support structure solution is formed by mixing a PLGA (poly(lactic-co-glycolic acid)) solution and a gelatin solution.

In the device for manufacture of polymeric micro-scaffolds according to the present invention, the PLGA solution is formed by mixing dichloromethane (DCM), PLGA (75:25), and a surfactant, and the gelatin solution is formed by mixing a PVA (poly vinyl alcohol) solution and gelatin.

In the device for manufacture of polymeric micro-scaffolds according to the present invention, the emulsifier solution is a 0.1-5% PVA solution.

In the device for manufacture of polymeric micro-scaffolds according to the present invention, the transporting gas supplied from the gas storage part is any one of nitrogen gas ($N_2$) and inactive gas.

In the device for manufacture of polymeric micro-scaffolds according to the present invention, the pressure controller controls the compression part so as to maintain a pressure of the transporting gas supplied to the first solution storage part at 3 kPa to 50 kPa.

In the device for manufacture of polymeric micro-scaffolds according to the present invention, the pressure controller controls the compression part so as to maintain a pressure of the transporting gas supplied to the second solution storage part at 3 kPa to 30 kPa.

In the device for manufacture of polymeric micro-scaffolds according to the present invention, the scaffold injector comprises a first pipe for supplying the emulsifier solution therethrough and a second pipe, arranged within the first pipe, for supplying the polymeric support structure solution therethrough, the second pipe having an end from which the polymeric support structure solution is released and which is located within the first pipe, whereby the scaffold dispersion is released from an end of the first pipe.

In the device for manufacture of polymeric micro-scaffolds according to the present invention, the first pipe is configured to supply the emulsifier solution to both sides of the second pipe, and the first pipe and the second pipe are each made of a stainless steel material.

In the device for manufacture of polymeric micro-scaffolds according to the present invention, the first solution storage part, the second solution storage part, and the scaffold production part are each adapted to have a stirrer installed therein.

Advantageous Effects

The device for manufacture of polymeric micro-scaffolds according to the present invention is advantageous in that the device can stably manufacture polymeric micro-scaffolds uniform in size in spite of changes of external conditions.

In addition, the device can manufacture polymeric micro-scaffolds on a mass scale for a long period of time and particularly, can control sizes of the scaffolds manufactured thereby as well as sizes of pores formed in the scaffolds.

DETAILED DESCRIPTION

Hereinafter, preferred embodiments of the present invention will be described in detail with reference to the accompanying drawings. However, in the following description, a detailed explanation of known related technologies may be omitted to avoid unnecessarily obscuring the subject matter of the present invention.

Since various variations may be performed on the exemplary embodiments according to the concept of the present invention and the embodiments of the present invention can be realized in a wide range of varied forms, specific exemplary embodiments of the present invention will be described herein in detail with reference to the appended drawings of the exemplary embodiments of the present invention. However, the present invention will not be limited only to the specific exemplary embodiments of the present invention which are disclosed herein. Therefore, it should be understood that the scope and spirit of the present invention can be extended to all variations, equivalents, and replacements in addition to the appended drawings of the present invention.

According to an aspect thereof, the present invention provides a device for manufacture of polymer micro-scaffolds.

Figure 1:
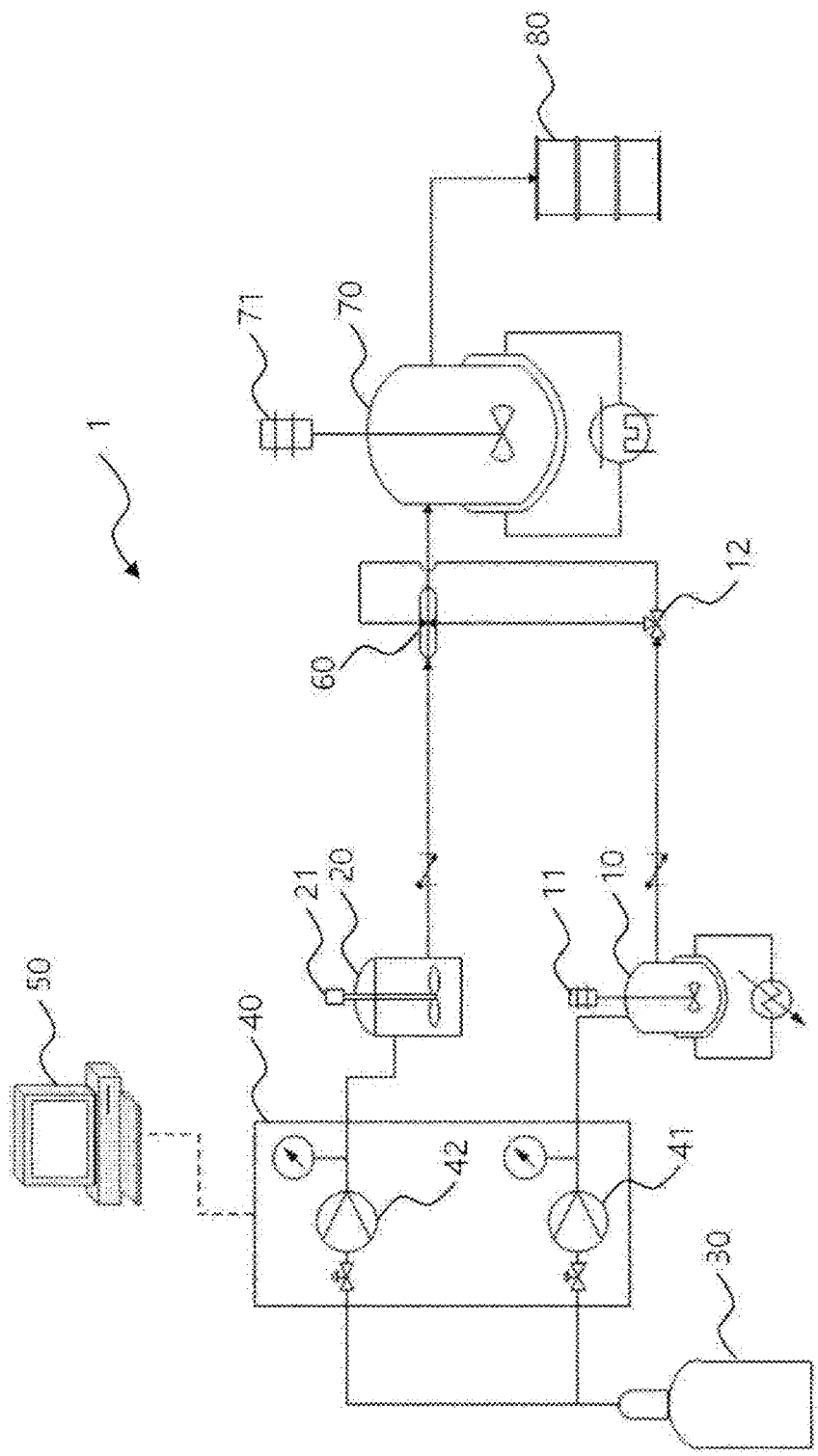
FIG. 1 is a schematic view showing the configuration of a device for manufacture of polymeric micro-scaffolds according to an embodiment of the present invention.
Figure 2:
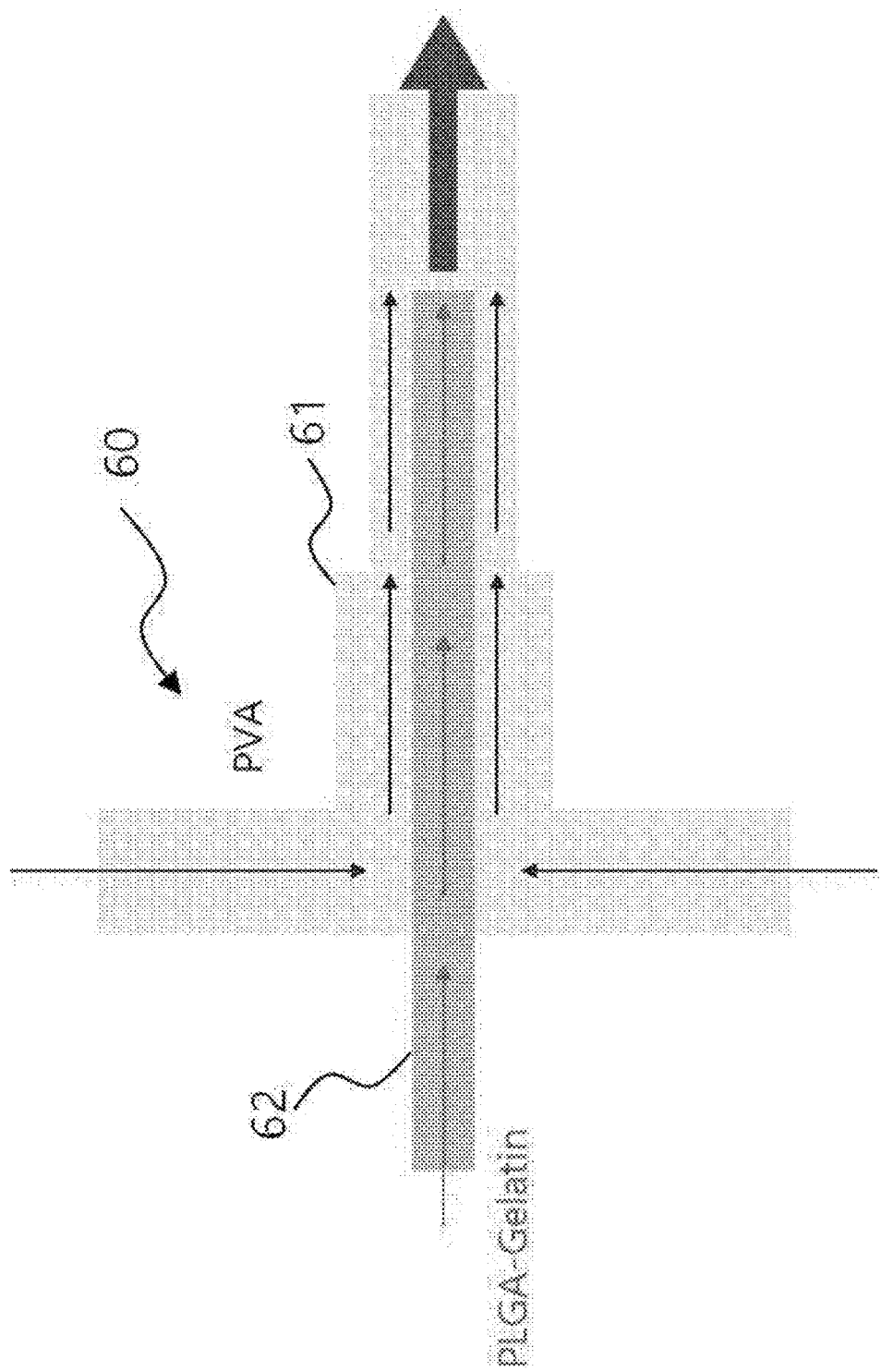
FIG. 2 is a schematic view showing the configuration of a scaffold injector as a component of the device for manufacture of polymeric micro-scaffolds.

FIG. 1 is a schematic view showing the configuration of a device for manufacture of polymeric micro-scaffolds according to an embodiment of the present invention and FIG. 2 is a schematic view showing the configuration of a scaffold injector as a component of the device for manufacture of polymeric micro-scaffolds.

With reference to the figures a device (1) for manufacture of polymeric micro-scaffolds according to an embodiment of the present invention comprises a first 1 solution storage part (10), a second solution storage part (20), a gas storage part (30), a compression part (40), a pressure controller (50), a scaffold injector (60), and a scaffold production part (70).

The first solution storage part (10), although not shown in detail, may have a dual vessel structure where a polymeric support structure solution is loaded to an inner vessel while deionized water contained in the outer vessel is heated to maintain a predetermined temperature of the inner vessel.

In this regard, the polymeric support structure solution may be formed by mixing a polymer solution and a biocompatible aqueous material solution useful for forming pores. The polymer solution may be made of a mixture of a polymer, dichloromethane (DCM), and a surfactant while the biocompatible aqueous material solution may be formed by mixing a biocompatible aqueous material and a PVA (polyvinyl alcohol) solution.

The pore size distribution in the scaffold can be controlled depending on the composition of the polymer solution-biocompatible aqueous material solution mixture (particle size/concentration/ratio of the biocompatible aqueous material, concentration of the surfactant, and mixing rpm).

So long as it is hydrophobic and is dissolved in a volatile organic solvent, any polymer may be used in the present invention. Examples of the polymer include PLGA (poly (lactic-co-glycolic acid)), PCL (poly-caprolactone), PLA (poly-lactic acid), PGA (poly-glutamic acid), PEG (polyethylene glycol), PLL (Poly-L-lysine), and copolymers thereof, but are not limited thereto.

Examples of the biocompatible aqueous material include, but are not limited to, gelatin, chitosan, hyaluronic acid, alginate, agarose, pectin, sodium carboxylate, chondroitin sulfate, and NaCl crystals.

By way of example, when the polymer is PLGA, a PLGA solution may be formed by mixing dichloromethane (DCM), PLGA (75:25), and a surfactant. When the biocompatible aqueous material is gelatin, it may be mixed with a PVA (polyvinyl alcohol) solution to give a gelatin solution.

Furthermore, the first solution storage part (10) comprises a stirrer (11) which is used to prevent the layer separation of the polymer solution-biocompatible aqueous material solution mixture, for example, PLGA-gelatin mixture.

The second solution storage part (20) may store an emulsifier solution. Examples of the emulsifier solution that may be stored in the second solution storage part (20) include PVA (poly vinyl alcohol), PVP (poly vinyl pyrrolidone), PEG (poly ethylene glycol), poloxamers, methylcellulose, Tween series, and/or mixture solutions thereof. Inside the second solution storage part (20) is arranged a stirrer (21) for stirring the emulsifier solution.

The gas storage part (30) communicates with both the first solution storage part (10) and the second solution storage part (20) via tubes or pipes and supplies to the first solution storage part 10 and the second solution storage part (20) a transporting gas for transporting the polymeric support structure solution and the emulsifier solution.

The transporting gas may comprise any one of inactive gases, such as nitrogen ($N_2$), helium (He), neon (Ne), argon (Ar), krypton (Kr), xenon (Xe), radon (Rn), etc.

The compression part (40) is to apply a pressure to the transporting gas provided for the first solution storage part (10) and the second solution storage part (20) and may comprise a micro pressure pump and may be arranged between the first solution storage part (10) and the gas storage part (30) and between the second solution storage part (20) and the gas storage part (30).

As shown in the figure, the compression part (40) may comprise a first compression module (41) and a second compression module (42) for applying a pressure to the transporting gas to supply the transporting gas to the first solution storage part (10) and the second solution storage part (20), respectively.

The pressure controller (50) can control the first compression module (41) and the second compression module (42) of the compression part (40) independently so that different pressures are applied to the transporting gas influent to the first solution storage part (10) and the second storage part (20). In this regard, the diameter distribution of the scaffolds can be controlled by a difference in pressure between the gases introduced into the containers.

That is, the higher is the pressure of the transporting gas supplied to the first solution storage part (10), the greater the diameter of the scaffolds is. On the other hand, a higher pressure of the transporting gas supplied to the second solution storage part (20) makes the diameter of the scaffold smaller. The ratio between the transporting gases supplied to the first solution storage part (10) and the second solution storage part (20) may range from 1:0.2 to 1:5.

The pressure controller (50) may control the first compression module (41) so as to maintain the pressure of the transporting gas supplied to the first solution storage part (10) at 3 kPa to 50 kPa and particularly at 10 kPa. In addition, the pressure controller (50) may control the second compression module (41) so as to maintain the pressure of the transporting gas supplied to the second solution storage part (20) at 3 kPa to 30 kPa and particularly at 5 kPa.

Although shown to comprise the first compression module (41) and the second compression module (42) in the figure, the device of the present invention may be configured to comprise multiple compression modules as needed.

The scaffold injector (60) receives the polymeric support structure solution and the emulsifier solution respectively supplied from the first storage part (10) and the second solution storage part (20) by the transporting gas and can release a scaffold dispersion resulting from coupling between the polymeric support structure solution and the emulsifier solution.

As shown in FIG. 2, the scaffold injector (60) may comprise a first pipe (61) communicating with the second solution storage part (20) and passing the emulsifier solution therethrough and a second pipe (62) communicating with the first solution storage part (10) and passing the polymeric support structure solution therethrough.

Particularly, the scaffold injector (60) may have a dual pipe structure in which the second pipe (62) is arranged inside the first pipe (61) while the end of the second pipe (62) from which the polymeric support structure solution is released is located within the first pipe (61), whereby the scaffold dispersion can be released from the end of the first pipe (61). The second pipe should be smaller in diameter than the first pipe.

In such a structure, the diameter distribution of the scaffold may be determined according to the diameters of the first pipe and/or the second pipe (62). The pipe diameter may range, for example, from 15 to 21 G (Gauge) (outer diameter: 0.82-1.83 mm, inner diameter: 0.51-1.37 mm) for the first pipe and, for example, from 19 to 34 G (Gauge) (inner diameter: 0.19-1.07 mm, outer diameter: 0.08-0.69 mm) for the second pipe.

In addition, the first pipe (61) may be configured to supply the emulsifier solution to both sides of the second pipe (62) so that the emulsifier solution is homogeneously supplied. Thus, the second solution storage part (20) may be connected to the scaffold injector (60) via a 3-way valve (12).

The first pipe (61) and the second pipe (62) may each be made of, for example, stainless steel, anti-corrosive metal (titanium (Ti), cobalt (Co), chromium (Cr), nickel (Ni), silver (Ag), gold (Ag) and an alloy thereof) or an antichemical resin (PVC (poly-vinyl chloride), PU (poly-urethane), PP (polypropylene), PTFE (poly-tetrafluoroethylene), PFA (perfluoroalkoxy alkane) and/or ETFE (ethylene tetra fluoro ethylene) so that the pipes can be prevented from clogging with the coagulation of the polymer solution-biocompatible aqueous material solution mixture, for example, PLGA-gelatin mixture.

Although not shown in detail, the scaffold production part (70) may have a dual vessel structure where the scaffold dispersion is loaded to an inner vessel while cooling water, for example, deionized water of 10° C. is contained in the outer vessel to maintain a predetermined temperature of the inner vessel. In this context, the pore size distribution in the scaffold can be controlled depending on the temperature of the inner vessel.

That is, the lower is the temperature of the inner vessel, the smaller the pore size is. At 0 to 25° C., the pore size can be controlled within 40 to 90 μm.

The scaffold production part (70) receives the scaffold dispersion released from the scaffold injector (60), removes the organic solvent and dispersion medium from the scaffold dispersion, and melts the internal gelatin particles to afford polymeric micro-scaffolds.

Furthermore, a stirrer (71) may be installed inside the scaffold production part (70) to prevent the scaffolds from aggregation, which may happen during the evaporation of the residual organic solvent and the washing process.

The polymeric micro-scaffolds produced in the scaffold production part (70) can be collected by the scaffold collector (80).

According to another aspect thereof, the present invention provides a method for manufacturing a large amount of polymeric micro-scaffolds.

The device (1) for manufacture of polymeric micro-scaffolds can stably manufacture polymeric micro-scaffolds uniform in size on mass scale and particularly, can drive in a continuous mode to allow the manufacture of polymeric micro-scaffolds on a large scale for a long period of time.

Thus, a description of overlapping contents in the manufacture of the polymeric micro-scaffolds is omitted to avoid excessive complexity of the present specification.

Experimental Example

1) Preparation of Mixture
(1) Preparation of PLGA Solution
In a 2-mL tube, 931 mL of dichloromethane (DCM), 70 mg of PLGA (75:25), and 15 µL of Span80 were mixed by vortexing for 7 minutes at 3200 rpm to prepare a PLGA solution.
(2) Preparation of Gelatin Solution
In 100-mL media bottle, 50 ml of a 1% PVA solution was put, followed by 3 g of gelatin. Subsequently, the media bottle was heated to 40° C. while dispersing the gelatin by stirring to prepare a gelatin solution.
(3) PLGA-Gelatin Mixture
In a 2-mL tube, 850 µL of the gelatin solution was added to the PLGA solution and mixed by vortexing at 3200 rpm for 2.5 minutes to form a PLGA-gelatin mixture.
(4) Preparation of 1% PVA Solution
In a media bottle, 400 mL of DI-water and 4 g of PVA were heated together at 200° C. while stirring at 500 rpm for 1 hour to dissolve PVA to prepare a 1% PVA Solution 2) Initial Setting
(1) 1.9 mL of the PLGA-gelatin mixture and 400 mL of the 1% PVA solution were loaded to respective vessels.
(2) 500 mL of DI-water was introduced into the production vessel as the scaffold production part.
(3) The PLGA-gelatin mixture was stirred at 1500 rpm and maintained at 35° C.
(4) In the production vessel, the DI-water was stirred at 250 rpm and maintained at 10° C.
3) Manufacture of Polymer Micro-Scaffold
(1) Using a micro pressure pump, the injection pressure of nitrogen ($N_2$) gas was adjusted and set to be 10 kPa for the PLGA-gelatin mixture and 5 kPa for the 1% PVA solution. With the aid of the injected nitrogen gas, the PLGA-gelatin mixture and the 1% PVA solution were transported to the scaffold injector.
(2) A scaffold dispersion was generated in the scaffold injector and sprayed through the scaffold injector into a production vessel to manufacture scaffolds.
(3) The scaffolds thus obtained were left for 4 hours in the production vessel (while stirring at a constant temperature) to evaporate residual organic solvents.
(4) In the production vessel, the stirring was stopped to settle down the scaffolds and the dispersion medium was removed, followed by adding 35° C. DI-water to dissolve the gelatin particles present inside the scaffolds (stirring for about 5 minutes).
(5) Step (3) was repeated 3-5 times to wash the polymeric micro-scaffolds until the dispersion medium became completely clear.
(6) The washed polymeric micro-scaffolds were settled down and transferred to a 30-ml collection vessel filled with DI-water.

Figure 3:
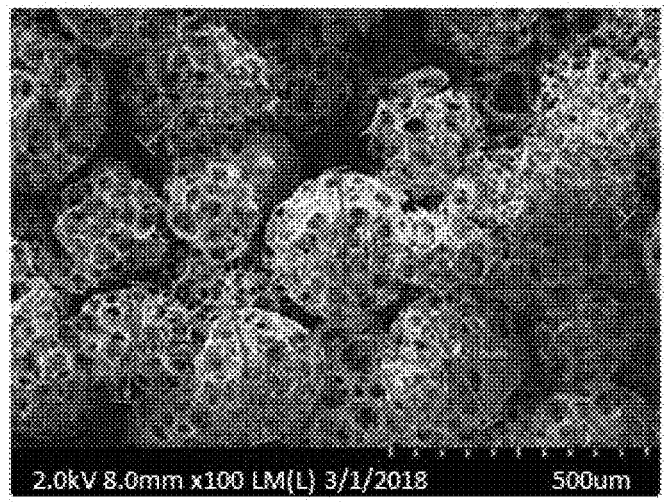
FIG. 3 shows microscopic images of polymeric micro-scaffolds different in size that were manufactured by the device for manufacture of polymeric micro-scaffolds according to an embodiment of the present invention.
Figure 3:
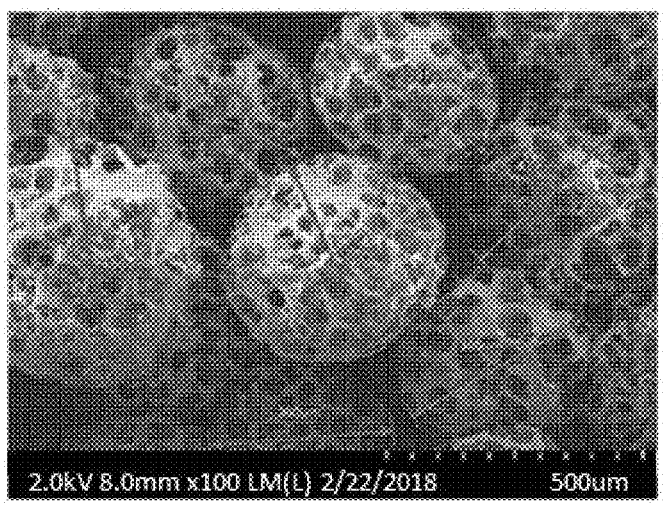
Figure 3:
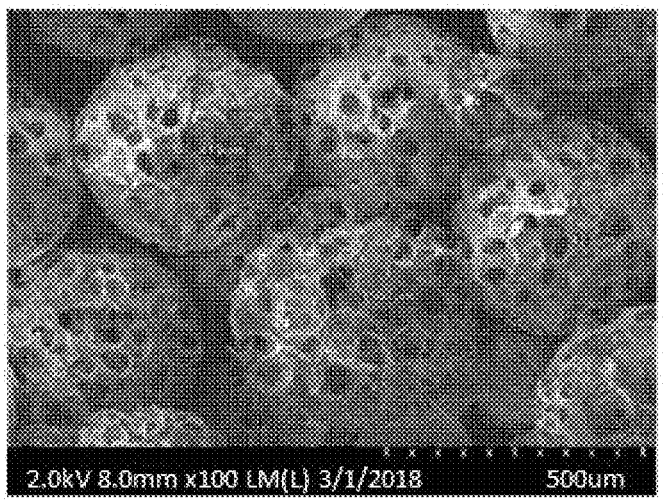
Figure 4:
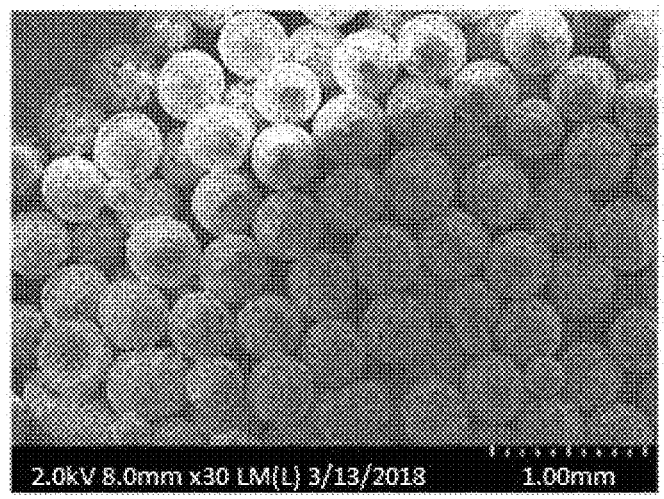
FIG. 4 shows microscopic images of polymeric micro-scaffolds different in pore size that were manufactured by the device for manufacture of polymeric micro-scaffolds according to an embodiment of the present invention.
Figure 4:
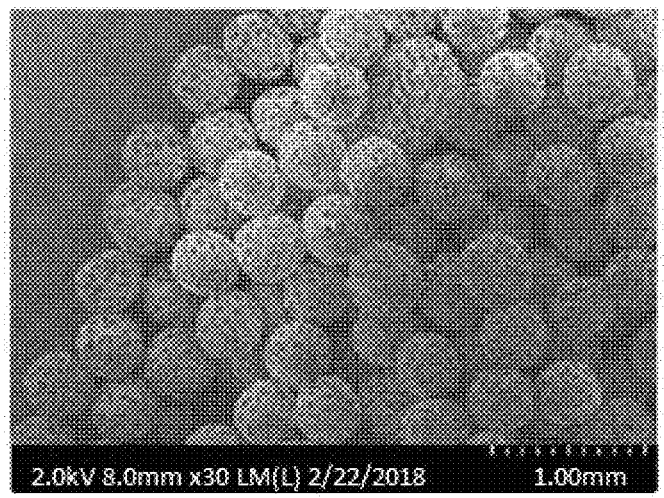
Figure 4:
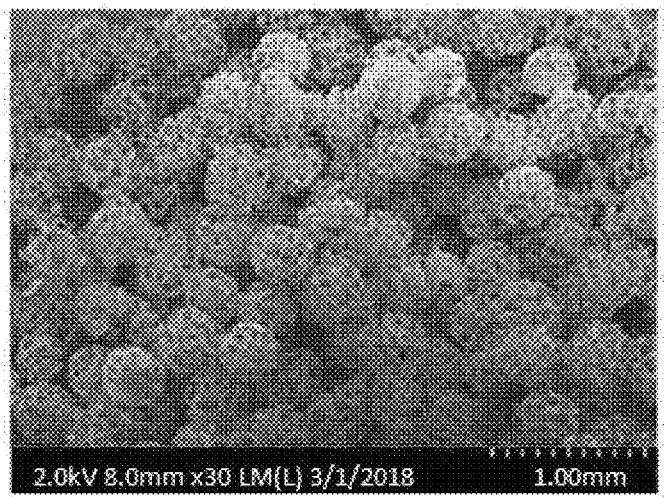

Through the manufacturing procedure described above, polymeric micro-scaffolds were manufactured as shown in FIGS. 3 and 4.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

DESCRIPTION OF REFERENCE NUMERALS

1: Device for manufacture of polymeric micro-scaffold
10: First solution storage part
20: Second solution storage part
30: Gas storage part
40: Compression part
50: Pressure controller
60: scaffold injector
70: scaffold production part

INDUSTRIAL APPLICABILITY

The present invention relates to a device for manufacturing a large amount of polymeric micro-scaffolds and, more particularly, to a device for manufacturing micro-scaffolds uniform in size on a mass scale.

What is claimed is:
1. A device for manufacture of polymeric micro-scaffolds, the device comprising:
a first solution storage part for storing a polymeric support structure solution;
a second solution storage part for storing an emulsifier solution;
a gas storage part, connected to both the first solution storage part and the second solution storage part, for providing a transporting gas for transporting the polymeric support structure solution and the emulsifier solution;
a compression part for applying a pressure to the transporting gas supplied to the first solution storage part and the second solution storage part;
a pressure controller for controlling the compression part so as to apply pressures to the transporting gas flowing into the first solution storage part and the second solution storage part, respectively;
a scaffold injector for receiving the polymeric support structure solution and the emulsifier solution respectively supplied by the transporting gas and releasing a scaffold dispersion resulting from coupling between the polymeric support structure solution and the emulsifier solution; and a scaffold production part for receiving the scaffold dispersion released from the scaffold injector, removing an organic solvent and a dispersion medium from the scaffold dispersion, and producing polymeric microscaffolds.

2. The device of claim 1, wherein the polymeric support structure solution is formed by mixing a PLGA (poly(lactic-co-glycolic acid)) solution and a gelatin solution.

3. The device of claim 2, wherein the PLGA solution is formed by mixing dichloromethane (DCM), PLGA (75:25), and a surfactant.

4. The device of claim 2, wherein the gelatin solution is formed by mixing a PVA (poly vinyl alcohol) solution and gelatin.

5. The device of claim 1, wherein the emulsifier solution is a 0.1-5% PVA solution.

6. The device of claim 1, wherein the transporting gas supplied from the gas storage part is any one of nitrogen gas ($N_2$) and inactive gas.

7. The device of claim 1, wherein the pressure controller controls the compression part so as to maintain a pressure of the transporting gas supplied to the first solution storage part at 3 kPa to 50 kPa.

8. The device of claim 1, wherein the pressure controller controls the compression part so as to maintain a pressure of the transporting gas supplied to the second solution storage part at 3 kPa to 30 kPa.

9. The device of claim 1, wherein the scaffold injector comprises a first pipe for supplying the emulsifier solution therethrough and a second pipe, arranged within the first pipe, for supplying the polymeric support structure solution therethrough, the second pipe having an end from which the polymeric support structure solution is released and which is located within the first pipe, whereby the scaffold dispersion is released from an end of the first pipe.

10. The device of claim 9, wherein the first pipe is configured to supply the emulsifier solution to both sides of the second pipe.

11. The device of claim 9, wherein the first pipe and the second pipe are each made of a stainless steel material.

12. The device of claim 1, wherein the first solution storage part, the second solution storage part, and the scaffold production part are each adapted to have a stirrer installed therein.

\* \* \* \* \*